Feb. 19, 1963 N. L. SELTZER Re. 25,332

DIAPER

Original Filed Aug. 26, 1959

United States Patent Office

Re. 25,332
Reissued Feb. 19, 1963

25,332
DIAPER

Norman L. Seltzer, Princeton, N.J., assignor to The Kendall Company, Boston, Mass., a corporation of Massachusetts Original No. 3,037,532, dated June 5, 1962, Ser. No. 836,225, Aug. 26, 1959. Application for reissue June 20, 1962, Ser. No. 205,484
8 Claims. (Cl. 139—383)

Matter enclosed in heavy brackets [ ] appears in the original patent but forms no part of this reissue specification; matter printed in italics indicates the additions made by reissue.

This invention relates to a diaper that is both ravel-resistant and corrugation-resistant and to the method for making the same.

A large proportion of the diapers now in use are either of two-ply or three-ply woven gauze or of birdseye weave in a single ply. The two-ply or three-ply woven gauze type diaper fabrics have separate plies or layers that are ordinarily interwoven along their longitudinal edges in a common selvage and united across the warp or machine direction of the fabric in a series of interwoven transverse strips. The individual diapers are formed by cutting or pinking the fabric along the center line of each such interwoven strip. The resulting diaper is not completely satisfactory since repeated washings result in raveling of the cut edges even though they are pinked, or in corrugating, or both.

Single ply diapers are made from a single set of warp yarns interwoven with a single set of filling yarns, most commonly in a float or "birdseye" weave to provide softness. Such diapers are likewise very susceptible to ravelling, and as sold they are always either hemmed or impregnated on the cut edges.

Some attempts have been made previously to eliminate this ravelling problem. Swartz, U.S. Patent No. 2,619,-089 for instance, teaches the impregnating and sealing of the cut edges with a material having the physical characteristics of rubber to prevent raveling. Since, however, in normal use diapers are subjected not only to varying amounts of physical wear but also to certain chemical actions and strenuous laundering treatment, often including repeated boiling, many sealing or impregnating materials commonly used with fabrics, as Swartz himself recognizes, are not suitable for sealing the cut edges of diapers. The arrangement also results in a diaper fabric having two different parts with distinctly different physical and chemical properties.

Of course, the simplest way to solve this raveling problem has been to hem these cut edges. When the diaper is hemmed, however, the edges contain several thicknesses of the fabric, and in use the superposition of such edges by folding results in there being more corpulence or bulk at certain areas of the diaper, with resulting discomfort to the wearer. Furthermore, the hems considerably increase the cost of producing the diaper because of the sewing involved. The hemmed edges also take much longer to dry than does the body portion of the diaper, delaying considerably the availability of the diapers for re-use after each washing.

Associated with the raveling has been the corrugation occuring in diapers as a result of washing, with the corrugation becoming more and more pronounced with each additional washing. These corrugations appear as a systematic series of waves or undulations running almost entirely in one dimension of the diaper, giving a pronounced parallel crimped effect to the diaper. They are generally formed with the lines of their ridges substantially parallel to the longer dimension of the diaper. The lines of the ridges of the corrugations are here considered to be the direction in which the corrugations "run."

Corrugations in diapers are caused by a lack of balance between warp yarns and filling yarns, whereby one set of yarns is dominant and the other set dependent. The dominant yarns may be either the warp yarns or the filling yarns. Dominance is determined by the yarn size, the twist multiple, and the number of yarns per inch. (The twist multiple equals the twist turns per inch of yarn divided by the square root of the yarn number in the cotton system.) Whenever the interaction of these three factors determines that the warp yarns are the dominant yarns, the filling yarns become the dependent yarns. Whenever these three factors determine that the filling yarns are the dominant yarns, the warp yarns become the corresponding dependent yarns. In weaving, warp yarns are subjected to tension and to mutual abrasion as the harnesses are raised and lowered. It is the usual practice, therefore, to twist the warp yarns more tightly than the filling yarns, in order to strengthen them. A standard warp twist for such fabrics is 4.75 or less, compared with an average filling twist of 3.50 (American Cotton Handbook, Second revised edition, Textile Book Publishers, New York, 1949: page 322. See also: Haven: "Mechanical Fabrics": page 122: Wiley & Sons, New York, 1932). Ordinarily in diapers warp twist ranges from about 3.8 to about 4.75 and filling twist ranges from 3.25 to about 4.0. Thus, diapers are usually so woven with respect to yarn size, twist multiple, and number of yarns per inch that the dominant yarns are the warp yarns and the dependent yarns are the filling yarns.

It is believed that the forces prevalent in the dominant yarns cause the corrugations which run across the dominant yarns and substantially parallel to the dependent yarns.

Normally, those diapers which have a rectangular shape are made with their long dimensions transverse to the warp or machine direction of the diaper fabric. Therefore, in most diapers, the corrugations are caused by the dominant warp yarns, with the corrugations running across the warp and substantially parallel to the filling. If diapers were made with their long dimensions parallel to the warp or machine direction of the diaper fabric, and if the dominant yarns were the filling yarns, the corrugations would run across the filling yarns and substantially parallel to the warp yarns.

Most of the corrugations in diapers could, of course, be eliminated by ironing after each washing. This, however, would not only be costly for diaper services but would also present an additional chore for those washing diapers at home.

In order to eliminate corrugations, various expedients have been tried. For one thing, the twist multiple of the warp yarns has been lowered without otherwise altering the fabric construction, and it has been found that the tendency to corrugate has correspondingly been lessened with each progressive lowering of the twist multiple of the warp yarns. When low twist multiple warp yarns are employed, however, the fabric is undesirably affected in that it tends to abrade faster. Thus its useful life is materially shortened, necessitating more frequent replacements. In addition, yarn spinning efficiencies and weaving efficiencies will be reduced unless longer staple fiber is used, causing an increase in production costs.

Other expedients, such as using S and Z twist yarns or balanced plied yarns in the same fabric, have been tried with limited amounts of success. These have not been found too satisfactory, however, because of the problems of spinning yarns of regular and reverse direction of twist and/or plied yarns in the same mill.

The designer of a diaper is faced with a number of conflicting requirements. A diaper is expected to be soft and fluffy, so that it is comfortable and non-chafing. It is expected to be highly absorbent, so that it performs properly in use. It should wash clean easily and dry quickly, which suggests that it be of a porous and open construction and not hemmed.

At the same time, the diaper should be durable so that it survives the abrasive effect of repeated laundering without holes appearing in the surface prematurely. It should be relatively stable in dimensions, so that it does not shrink excessively. The yarns should be so chosen or interwoven that the diaper does not develop objectionable corrugations in laundering. Nor should the pinked edges of the diaper ravel. In addition, since the diaper industry is highly competitive, all these desirable properties should be brought about at maximum economy and efficiency.

The above requirements suggest conflicting solutions. Therefore, modern diapers are a compromise. Up to now, this compromise has been made in a haphazard fashion, because the interrelation between the structural factors involved has never been clearly understood or set forth.

Consumer demand dictates certain minimum "cosmetic" or "esthetic" requirements of softness, absorbency, and porosity in diapers. This in general had led to gauze diapers being made in a count of from 36 to 42 warp yarns and 30 to 38 filling yarns per layer, both sets of yarns ranging in size from 24's to 37's. Twist multiples in both sets of yarns may range from about 3.25 to about 4.75, as set forth above.

Within the above ranges, there is tremendous variation in the amounts of corrugation and raveling that may be encountered. These "performance factors," as they may be called, depend on the structural constants which are dictated by the above-mentioned "cosmetic" requirements. But up to now, the nature of that dependency has never been accurately appreciated or expressed.

The principal object of the invention is to provide a diaper fabric that will not ravel along its cut edges without being hemmed or bonded and that will not corrugate at its body portion even after many repeated washings. A further object of the invention is to provide a novel diaper fabric that will neither ravel nor corrugate without the employment of S and Z twist or plied yarns in the same fabric.

This invention resulted from very considerable and exhaustive study and only after tedious and painstaking experimental investigation in the course of which, in order to accomplish the above objects, there were made various surprising discoveries relating to the several interdependent factors which influence raveling and corrugating.

Diapers have been made which resisted corrugation. Other diapers have also been made which resisted raveling. Sometimes the experimentation was more successful than at other times. Never to my knowledge, however, has an acceptable and economical multi-layer gauze diaper been produced which simultaneously prevented both corrugation and raveling. Yet, the variation of my new diaper from the regular commercial diaper is not a drastic one nor an uneconomical one. It represents chiefly the recognition of the function of two factors heretofore not appreciated, i.e., the number of ends and picks in one repeat and the average number of interlacings in one repeat. By "repeat" is meant the disposition of warp and filling yarns relative to each other in the smallest element of structure before such a disposition becomes repetitive. The repeat is therefore the basic unit of a weave and it is the number of yarns required before the weave starts over again. The number of warp ends and picks in the repeat may be equal or unequal as explained with reference to the structure above, but in every case, the complete repeat must be in rectangular form.

An interlacing occurs whenever one warp or filling yarn goes over or under one filling or warp yarn respectively. The number of interlacings for each yarn in the repeat is counted first in one weave direction, let us say warpwise, and the sum then divided by the number of warp ends in the repeat; then the number of interlacings is counted for each yarn in the repeat in the other weave direction, fillingwise, and the sum then divided by the number of filling yarns in the repeat. The two numbers so resulting are then added, giving the average number of interlacings in one repeat.

The effect of these heretofore unappreciated factors, when put in proper relation with the other already known factors, enabled me to provide diapers in which both corrugation and raveling are simultaneously eliminated. These various factors when brought into mathematical relation with each other enabled me to set up formulae which define a minimum interaction and interrelation among these factors. These formulae provide for a diaper construction in which both corrugation and raveling are effectively controlled with an economy and efficiency of operation not heretofore realized. The formulae predict accurately just what effect a change in one of the factors in the diaper construction will have on the stability of the diaper. They also enable a diaper designer to make any desired changes with complete confidence in how far the counter-balancing changes have to go.

By properly applying these discoveries in required overall tightness of yarns, in yarn size and twist multiple selection, in weave design, and in weaving, one can produce a diaper which is characterized by the absence of raveling and corrugations even though not hemmed or otherwise bonded at its pinked edges and even though no S and Z twist or plied yarns are employed in the same diaper. Furthermore, by applying these discoveries, one can produce a diaper fabric substantially all of unidirectional twist yarns on standard textile equipment and at no notable increase in manufacturing cost over the cost of otherwise similar diaper fabrics of like weight.

The invention will be explained by way of illustration as it applies to a woven textile article such as a cotton diaper. Those low-count diapers known as gauze diapers have been made, by way of example, with the number of yarns per inch ranging from about 31 to about 62 per layer in the warp and from about 21 to about 50 per layer in the filling, and with yarn sizes ranging from about 16/1 to 40/1 in both the warp and the filling. Single-layer birdseye diapers may be commonly made from fabrics employing warp yarns approximately from about 20/1 to about 40/1 yarn sizes and from about 12/1 to about 40/1 yarn sizes in the filling. The warp count in these single-layer diapers may be as low as 62 per inch and as high as 124 per inch, and the pick count may be as low as 21 per inch and as high as 70 per inch. The twist multiples of the yarns in the single-layer diapers may range from about 3.25 to about 4.75 as described above.

This invention will be more fully understood from the following detailed description, reference being had to the accompanying drawing. It is to be understood, however, that the drawing must be viewed only as illustrative of the invention and that the invention is not limited thereto, except as may be specifically set forth in the appended claims.

For convenience of illustration, the number of ends and picks per inch shown in these figures is less than in the actual diaper.

Figure 2:
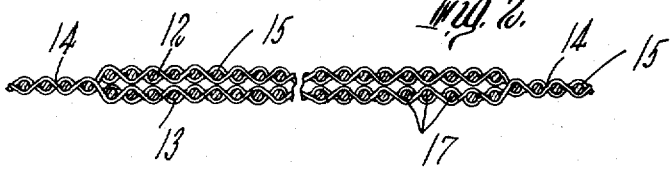
FIG. 2 is a cross-section of the same diaper on line 2—2 of FIG. 1, showing portions of the body and of the pinking bars wherein the body portion 11 is of two layers.
Figure 3:
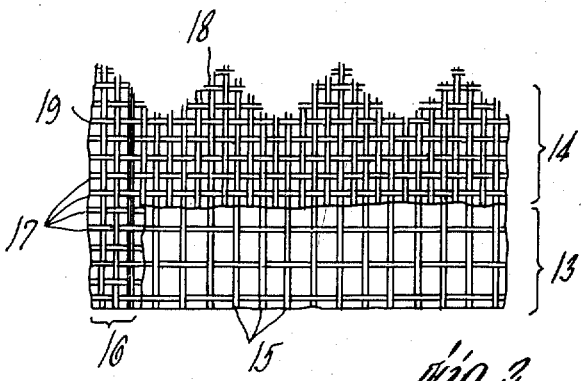
FIG. 3 is a plan view of a portion of a corner of the diaper shown in FIG. 2, on an enlarged scale, with the top layer of the body cut away.

The reference numeral 10 represents a diaper having a body portion 11, with single-layer pinking bar portions 14 and single-layer selvage portions 16. As shown in FIG. 2, in the case of a multi-ply gauze diaper, the body portion 11 is composed of two plies 12 and 13, inter-woven at the selvages and at the pinking bar portions. As shown in FIG. 3, the diaper is woven with warp yarns 15, which are continuous through both the body and the pinking bar portions, and filling yarns 17, and is pinked as at 18 in the bar portions 14. These bar portions normally extend transversely across the warp or machine direction of the fabric and are between one and two inches in width. The pinking or cutting produces the zig-zag or scalloped pattern 18. The first continuous uncut filling yarn at the base of this pattern is designated by the numeral 19.

Figure 1:
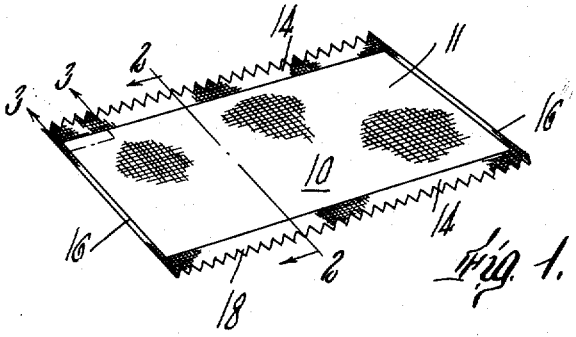
FIG. 1 is a perspective view of a diaper embodying the invention.

The diapers of FIGURES 1, 2, and 3 show a plain weave, which is a 2 x 2 structure in one repeat having an average of two interlacings in both the warp and filling direction. A 2 x 2 structure is one repeat in a structure which is made up of two warp and two filling yarns respectively. Similarly, a 6 x 6 structure is made up of six warp and six filling yarns, while a 6 x 8 structure is constituted of six warp and eight filling yarns respectively.

With respect to the size and pick and end count of the yarns, the diaper 10 may be woven in a wide variety of constructions, depending upon the particular use for which it is intended. One typical commercial product of the invention is a two-layer plain weave gauze diaper in which bleached cotton yarns, which may be as heavy as 24.5/1 with twist multiples 3.80, are used in both the warp and filling. The number of yarns per inch in each layer of the body portion of the diaper is 45 x 34. The construction of the pinking bar is 90 x 60.

Weaves other than that above noted may be employed in two-layer diapers, as, for example, a 42 x 34 or 34 x 34 or 45 x 36 or 40 x 36 in each layer of the body portion of the diaper. The yarn size in these weaves may be as heavy as 16/1 and may be as fine as 40/1, although yarn sizes between 22/1 and 30/1 are generally preferred. It will be understood, however, that the invention is not limited in its application to the particular fabrics mentioned. The two-layered gauze diaper may have a broken twill weave, or other fancy or novelty weave, in one or both faces. It must be recognized, however, that the degree of interlacing between yarns is a vital function in practising my invention, as set forth below. Therefore, in deviating from a plain weave, I may have to make adjustments in the other factors in my formula in order to meet the standards I have found essential.

In the case of a single-layer diaper, the body portion 11 of FIG. 1 will be a single layer made up of one layer of warp yarns and one layer of filling yarns. As set forth above, the warp count in a single layer diaper may vary from 62 to 124, and the filling count from 21 to 70. The body weave may be plain, but is preferably birdseye or other non-plain weave such as a broken twill. For convenience, wherever the word birdseye occurs in the specification or the claims, it refers to a weave other than a plain weave.

The twist multiple of the yarns employed in the industry varies between 3.25 and 4.75, depending upon the staple length of the fibers, and depending on whether the yarn is to be used in the warp or the filling. Mills usually are reluctant to employ a twist multiple below 3.25 because with low twist multiple yarns, the looms become progressively less workable and the spinning and weaving efficiencies become reduced sufficiently as to substantially increase cost of production. Furthermore, a product made of low twist multiple yarns has a shorter useful life, since it possesses less resistance to abrasive force. It is usually economically prohibitive, and, from a production standpoint, unnecesary, to go above 4.75 in the twist multiple.

My observations in such diapers afforded a basis for the derivation of mathematical formulae which, as a practical matter, give a guide for successful application and use of the invention in the actual manufacture of non-corrugating and non-raveling diaper fabrics. These formulae define the interrelation of the warp and filling yarns in any particular weave with respect to index numbers, yarn size, twist multiple, number of ends and picks in one repeat, average number of interlacings in one repeat, picks per inch and sley in one layer. The range of index numbers, designated as K for the corrugation index number, and as Q for the raveling index number, has been determined after a long series of experimental investigations based upon the underlying theoretical reasoning. These investigations have defined the approximate ranges of the corrugation index number K which must be within the range from about .30 to about .45 and of the raveling index number Q which must be within the range from about 1.10 to about 1.50. In general, the higher the index numbers, the less open will be the fabric; and in commercial diapers it is preferable to utilize K index numbers between .30 and .34 and Q index numbers between 1.10 and 1.35. The formula relating to corrugation in the body portion is as follows:

$$P=\frac{K\left(\frac{T_w}{3.80}\right)\times F\times R}{R+I\left(\frac{S}{W}\right)}$$

where:

P is the number of picks or filling yarns per inch required in one layer of the body portion, K is the corrugation index number, $T_w$ is the twist multiple of the warp yarns, F equals the maximum number of filling yarns that can lie side by side in one inch, R equals the number of ends and picks in one repeat, I equals the average number of interlacings in one repeat, S equals the number of warp ends per inch in one layer of the body portion, W equals the maximum number of warp yarns that can lie side by side in one inch.

W and F are equal to the function of a constant times the square root of the yarn size of the warp or filling yarns respectively (all yarn sizes referring to the cotton system). The constant is 28 for cotton, spun viscose, spun acetate, spun silk, linen, and for fine worsted. To find the constants for other fibers, see Lloyd H. Jackson's Yarn and Cloth Calculations (New York 1946, Textile Book Publishers, Inc., New York 16, New York), page 44.

By solving this formula for P, all other factors having been determined to produce a diaper having the desired properties, one obtains the minimum number of picks per inch required in the body of the diaper which will effectively resist corrugations.

This formula may be solved for the corrugation index figure K as follows:

$$K=\frac{P\left[R+I\left(\frac{S}{W}\right)\right]}{\left(\frac{T_w}{3.80}\right)\times F\times R}$$

The formula relating to raveling in the single-layer pinking bar portions is as follows:

$$E=\frac{Q\times R_p\times W}{R_p+I_p\left(\frac{A}{56}\right)}$$

where:

E represents the minimum number of warp ends per inch required in the pinking bar portions to make them ravel resistant, Q is the raveling index number, $R_p$ equals the number of ends and picks in one repeat in the bar portions, W equals the maximum number of warp yarns that can lie side by side in one inch, $I_p$ equals the average number of interlacings in one repeat in the bar portions, A equals the actual picks per inch at the bar portions, and 56 is a constant.

This formula may be solved for the raveling index number Q as follows:

$$Q=\frac{E\left[R_p+I_p\left(\frac{A}{56}\right)\right]}{R_p\times W}$$

If, because of weight requirements, it is desirable to lower the warp count of the diapers below that designated by E in the formula, raveling in the pinking bar portions may still be eliminated by increasing the pick count in the bar portions in accordance with the formula. Such additional picks in the bar portions may then be conveniently jammed in by the utilization of the pinch-pick mechanism.

Whenever the K and/or Q formulae give an index number that is not within the ranges indicated, one may change any one or more of the factors in the formulae to bring the index number within those ranges.

By "raveling" is meant the shredding or detachment from the diaper of the continuous uncut yarns adjacent the pinked edges (as illustrated by 19 in FIG. 3). "Pinking" is a method of cutting the edges of the diaper in scalloped or zig-zag form; the cutting is done by a pinking machine or specially made shears. By "pinking bar" is meant the interwoven strip adjacent the diaper body which is cut in scalloped or zig-zag pattern. Whenever these terms occur, either in the specification or in the claims, they should be interpreted in the sense of these definitions.

Some examples of the invention are as follows:

EXAMPLE I

It was desired to produce two-layer, plain weave cotton gauze diapers that resisted raveling in the bar portions when pinked though free of resin and resisted corrugation in the body portion though substantially all of the warp and filling yarns were of unidirectional twist.

A weave of 45 x 34 in each layer of the body was used with both warp and filling yarns being of the size of 24.5/1 with twist multiples of 3.80. The interwoven pinking bar portions had a weave of 90 x 56. The diaper weighed .1536 pound per yard and measured 40 x 21 inches, with the longer dimension being in the filling direction.

Insertion of these numbers in the fraction $$\frac{P\left[R+I\left(\frac{S}{W}\right)\right]}{\left(\frac{T_w}{3.80}\right)\times F\times R}$$

gave a corrugation index number of .33 which was within the desired range.

Insertion of the numbers applicable to the interwoven pinking bar portions in the fraction $$\frac{E\left[R_p+I_p\left(\frac{A}{56}\right)\right]}{R_p\times W}$$

produced a raveling index number of 1.29 which again was within the desired range.

The diaper thus produced neither corrugated nor raveled, even after repeated washings.

EXAMPLE II

It was desired to produce two-layer, plain weave cotton gauze diapers that resisted both raveling in the interwoven pinking bar portions though free of resin and corrugations in the body portion though substantially all of the warp and filling yarns were of unidirectional twist.

A weave of 45 x 36 in each layer of the body portion was used with both the warp and filling yarns being of the size of 30/1 with twist multiples of 3.80. The weave at the single-layer bar portions was 90 x 62. The diaper weighed .1285 pound per yard and measured 40 x 21 inches, with the longer dimension being in the filling direction.

Insertion of these numbers in the fraction $$\frac{P\left[R+I\left(\frac{S}{W}\right)\right]}{\left(\frac{T_w}{3.80}\right)\times F\times R}$$

gave a corrugation index number of .30 which was within the desired range.

Insertion of the numbers pertaining to the interwoven pinking bar portions in the fraction $$\frac{E\left[R_p+I_p\left(\frac{A}{56}\right)\right]}{R_p\times W}$$

produced a raveling index number of 1.24 which also was within the desired range.

The diaper thus produced neither corrugated nor raveled, even after repeated washings.

EXAMPLE III

It was desired to produce a single-layer birdseye-weave diaper (FIG. 1) that would not corrugate in the body nor ravel along the pinked edge in laundering, even though the diaper were free of impregnants and all yarns were of one direction of twist.

Figure 4:
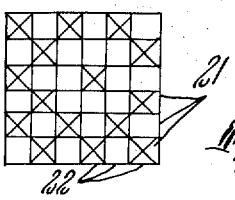
FIG. 4 is a draft diagram of the body portion of a single-layered birdseye diaper such as shown in FIG. 1.

To satisfy weight and absorbency requirements, cotton yarns of 23's warp and 30's filling were selected, with twist multiples of 3.80 in both sets of yarns. A sley of 84 with a pick count of 32 yarns per inch was selected to form a birdseye weave body. The weave structure employed, as shown in FIG. 4, had six warp yarns 22 and six filling yarns 21 per repeat, and the floats were so chosen that the average number of interlacings per repeat was eight. The ratio of the average number of interlacings per repeat to the aggregate number of warp and filling yarns per repeat was therefore 8 to 12, or 0.67.

Calculation of the corrugation index showed that it was approximately 0.3, so that the body of the diaper would not corrugate.

Calculation of the raveling index, however, showed that it was too low. Even changing the weave from birdseye to plain weave in the pinking bar, thereby increasing the interlacing ratio to its maximum, gave a raveling index of only 0.98.

To prevent raveling, therefore, the weave pattern was altered so that the pick count of 32 per inch in the body of the diaper was increased to 60 per inch, in a plain weave, in the two-inch wide pinking bar section. The raveling index was thereby increased to 1.3.

The diaper as finally designed and produced showed no corrugation nor raveling on repeated laundering.

The invention is also applicable to diaper fabric constructions or more than two layers, as well as to single and double layer constructions that are woven in accordance with the above-described mathematical formulae so that, when the formulae are solved for the corrugation and raveling index numbers, the resulting values are within the ranges indicated. All the diaper constructions woven in accordance with the formulae would likewise resist or prevent both corrugation and raveling though free of resin and embodying only unidirectional twist yarns.

It will be appreciated by those skilled in the art, that the tendency toward corrugation or raveling will vary with the usage to which the diaper is put. It is possible, therefore, that circumstances may allow the K index or Q index alone to be utilized in the construction of a diaper, without departing from the principles of the invention.

This application is a continuation-in-part of my application Serial Number 742,563 of June 17, 1958, now abandoned.

Having thus described my invention, what I claim is:

1. A diaper comprising warp and filling yarns substantially all of unidirectional twist, the size of said yarns being from about 16/1 to about 40/1 and having twist multiples ranging from about 3.25 to about 4.0 in the filling and from about 3.8 to about 4.75 in the warp, said diaper having a multi-layer body portion and single-layer pinking bar portions, the warp yarns and the filling yarns being so related as to yarn size, twist multiple, number of ends and picks in one repeat, average number of interlacings in one repeat, picks per inch and sley in one layer so as to give an index number within the range from about .30 to about .45 in the fraction relating to each individual layer of the body $$\frac{P\left[R+I\left(\frac{S}{W}\right)\right]}{\left(\frac{T_w}{3.80}\right)\times F\times R}$$

where P equals the picks per inch in one layer, R equals the number of ends and picks in one repeat, I equals the average number of interlacings in one repeat, S equals the warp ends per inch in one layer, W equals the maximum number of warp yarns that can lie side by side in one inch, $T_w$ equals the twist multiple of the warp yarns, F equals the maximum number of filling yarns that can lie side by side in one inch, and an index number within the range from about 1.10 to about 1.50 in the fraction relating to the single-layer pinking bar portions $$\frac{E\left[R_p+I_p\left(\frac{A}{56}\right)\right]}{R_p\times W}$$

where E equals the warp ends per inch in the pinking bar portions, $R_p$ equals the number of ends and picks in one repeat in the bar portions, $I_p$ equals the average number of interlacings in one repeat in the bar portions, A equals the actual picks per inch at the bar portions, and W equals the maximum number of warp yarns that can lie side by side in one inch.

2. A diaper comprising warp and filling yarns substantially all of unidirectional twist, the size of said yarns being from about 12/1 to about 40/1 and having twist multiples ranging from about 3.25 to about 4.0 in the filling and from about 3.8 to about 4.75 in the warp, said diaper having a body portion and pinking bar portions, the warp yarns and the filling yarns being so related as to yarn size, twist multiple, number of ends and picks in one repeat, average number of interlacings in one repeat, picks per inch, and warp ends per inch so as to give an index number within the range from about .30 to about .45 in the fraction relating to the body portion $$\frac{P\left[R+I\left(\frac{S}{W}\right)\right]}{\left(\frac{T_w}{3.80}\right)\times F\times R}$$

where P equals the picks per inch, R equals the number of ends and picks in one repeat, I equals the average number of interlacings in one repeat, S equals the warp ends per inch, W equals the maximum number of warp yarns that can lie side by side in one inch, $T_w$ equals the twist multiple of the warp yarns, F equals the maximum number of filling yarns that can lie side by side in one inch, and an index number within the range from about 1.10 to about 1.50 in the fraction relating to the pinking bar portions $$\frac{E\left[R_p+I_p\left(\frac{A}{56}\right)\right]}{R_p\times W}$$

where E equals the warp ends per inch in the pinking bar portions, $R_p$ equals the number of ends and picks in one repeat in the bar portions, $I_p$ equals the average number of interlacings in one repeat in the bar portions, A equals the actual picks per inch at the bar portions, and W equals the maximum number of warp yarns that can lie side by side in one inch.

3. A diaper comprising cellulosic warp and filling yarns substantially all of unidirectional twist, the size of said yarns being of about 16/1 to about 40/1 and having twist multiples ranging from about 3.25 to about 4.0 in the filling and from about 3.8 to about 4.75 in the warp, said diaper having a multi-layer body portion and single-layer pinking bar portions, the warp yarns and the filling yarns being so related as to yarn size, twist multiple, number of ends and picks in one repeat, average number of interlacings in one repeat, picks per inch, and warp ends per inch so as to give an index number of about .30 in the fraction relating to the body portion $$\frac{P\left[R+I\left(\frac{S}{W}\right)\right]}{\left(\frac{T_w}{3.80}\right)\times F\times R}$$

where P equals the picks per inch in one layer, R equals the number of ends and picks in one repeat, I equals the average number of interlacings in one repeat, S equals the warp ends per inch in one layer, W equals the maximum number of warp yarns that can lie side by side in one inch, $T_w$ equals the twist multiple of the warp yarns, F equals the maximum number of filling yarns that can lie side by side in one inch, and an index number of about 1.24 in the fraction relating to the pinking bar portions $$\frac{E\left[R_p+I_p\left(\frac{A}{56}\right)\right]}{R_p\times W}$$

where E equals the warp ends per inch in the pinking bar portions, $R_p$ equals the number of ends and picks in one repeat in the bar portions, $I_p$ equals the average number of interlacings in one repeat in the bar portions, A equals the actual picks per inch at the bar portions, and W equals the maximum number of warp yarns that can lie side by side in one inch.

4. A diaper comprising warp and filling yarns substantially all of unidirectional twist, the size of said yarns being from about 12/1 to about 40/1, and having twist multiples ranging from about 3.25 to about 4.0 in the filling and from about 3.8 to about 4.75 in the warp, said diaper having a single-layer birdseye body portion and at least one single-layer pinking bar portion, said diaper likewise having an index number within the range from about 1.10 to 1.50 in the fraction relating to said bar portion $$\frac{E\left[R_p+I_p\ \frac{A}{56}\right]}{R_p\times W}$$

where E=the warp ends per inch in the pinking bar portions, $R_p$ equals the number of ends and picks in one repeat in the bar portions, $I_p$ equals the average number of interlacings in one repeat in the bar portion, A equals the actual picks per inch in the bar portion, and W equals the maximum number of warp yarns that can lie side by side in one inch.

5. The diaper according to claim 4 wherein the index number is at least 1.24.

*6. A diaper comprising warp and filling yarns, the size of said yarns being from about 12/1 to about 40/1,*

*and having twist multiples ranging from about 3.25 to about 4.0 in the filling and from about 3.8 to about 4.75 in the warp, said diaper having a single-layer birdseye body portion and at least one single-layer pinking bar portion, said diaper likewise having an index number within the range from about 1.10 to 1.50 in the fraction relating to said bar portion,*

$$\frac{E\left[R_p+I_p\left(\frac{A}{56}\right)\right]}{R_p\times W}$$

*where E equals the warp ends per inch in the pinking bar portions, $R_p$ equals the number of ends and picks in one repeat in the bar portions, $I_p$ equals the average number of interlacings in one repeat in the bar portion, A equals the actual picks per inch in the bar portion, and W equals the maximum number of warp yarns that can lie side by side in one inch the number of picks per inch A in the bar portion of said diaper being greater than the number of picks per inch in the body portion of said diaper.*

*7. A diaper comprising warp and filling yarns, the size of said yarns being from about 16/1 to about 40/1 and having twist multiples ranging from about 3.25 to about 4.0 in the filling and from about 3.8 to about 4.75 in the warp, said diaper having a single-layer body portion and single-layer pinking bar portions, the warp yarns and the filling yarns being so related as to yarn size, twist multiple, number of ends and picks in one repeat, average number of interlacings in one repeat, picks per inch and sley in one layer so as to give a corrugation index number within the range from about .30 to about .45 in the fraction relating to each individual layer of the body*

$$\frac{P\left[R+I\left(\frac{S}{W}\right)\right]}{\left(\frac{T_w}{3.80}\right)\times F\times R}$$

*where P equals the picks per inch in one layer, R equals the number of ends and picks in one repeat, I equals the average number of interlacings in one repeat, S equals the warp ends per inch in one layer, W equals the maximum number of warp yarns that can lie side by side in one inch, $T_w$ equals the twist multiple of the warp yarns, F equals the maximum number of filling yarns that can lie side by side in one inch, and a raveling index number within the range from about 1.10 to about 1.50 in the fraction relating to the single-layer pinking bar portions*

$$\frac{E\left[R_p+I_p\left(\frac{A}{56}\right)\right]}{R_p\times W}$$

*where E equals the warp ends per inch in the pinking bar portions, $R_p$ equals the number of ends and picks in one repeat in the bar portions, $I_p$ equals the average number of interlacings in one repeat in the bar portions, A equals the actual picks per inch at the bar portions, and W equals the maximum number of warp yarns that can lie side by side in one inch the number of warp ends per inch being of sufficient magnitude to provide a corrugation index within said range of .30 to about .45 in the body portion of said diaper and insufficient to provide a raveling index of at least about 1.10 in the bar portion of said diaper, the number of picks per inch A in the bar portion of said diaper being greater than the number of picks per inch in the body portion of said diaper.*

*8. A diaper comprising cellulosic warp and filling yarns, the size of said yarns being of about 16/1 to about 40/1 and having twist multiples ranging from about 3.25 to about 4.0 in the filling and from about 3.8 to about 4.75 in the warp, said diaper having a single-layer body portion and single-layer pinking bar portions, the warp yarns and the filling yarns being so related as to yarn size, twist multiple, number of ends and picks in one repeat, average number of interlacings in one repeat, picks per inch, and warp ends per inch so as to give a corrugation index number of about .30 in the fraction relating to the body portion*

$$\frac{P\left[R+I\left(\frac{S}{W}\right)\right]}{\left(\frac{T_w}{3.80}\right)\times F\times R}$$

*where P equals the picks per inch in one layer, R equals the number of ends and picks in one repeat, I equals the average number of interlacings in one repeat, S equals the warp ends per inch in one layer, W equals the maximum number of warp yarns that can lie side by side in one inch, $T_w$ equals the twist multiple of the warp yarns, F equals the maximum number of filling yarns that can lie side by side in one inch, and a raveling index number of about 1.24 in the fraction relating to the pinking bar portions*

$$\frac{E\left[R_p+I_p\left(\frac{A}{56}\right)\right]}{R_p\times W}$$

*where E equals the warp ends per inch in the pinking bar portions, $R_p$ equals the number of ends and picks in one repeat in the bar portions, $I_p$ equals the average number of interlacings in one repeat in the bar portions, A equals the actual picks per inch at the bar portions, and W equals the maximum number of warp yarns that can lie side by side in one inch the number of warp ends per inch being of sufficient magnitude to provide a corrugation index within said range of about .30 in the body portion of said diaper and insufficient to provide a raveling index of at least about 1.24 in the bar portion of said diaper, the number of picks per inch A in the bar portion of said diaper being greater than the number of picks per inch in the body portion of said diaper.*

References Cited in the file of this patent or the original patent

UNITED STATES PATENTS

| | | |
|---|---|---|
| Re. 24,139 | Jamison et al. | Apr. 10, 1956 |
| 2,713,359 | Dangel et al. | July 19, 1955 |
| 2,845,069 | Jamison et al. | July 29, 1958 |